United States Patent [19]

Martel et al.

[11] Patent Number: 4,642,372

[45] Date of Patent: Feb. 10, 1987

[54] NOVEL PROCESS FOR PREPARATION OF 1-FURENYL-2,2-DIMETHYL-CYCLOPROPANE CARBOXYLIC ACID DERIVATIVES

[75] Inventors: Jacques Martel, Bondy; Jean Tessier, Vincennes; Jean-Pierre Demoute, Montreuil-sous-Bois, all of France

[73] Assignee: Roussel Uclaf, Paris, France

[21] Appl. No.: 760,313

[22] Filed: Jul. 29, 1985

Related U.S. Application Data

[63] Continuation of Ser. No. 300,927, Sep. 10, 1983, abandoned.

[30] Foreign Application Priority Data

Sep. 24, 1980 [FR] France .................. 80 20476

[51] Int. Cl.$^4$ ........................................ C07C 69/757
[52] U.S. Cl. ........................ 560/124; 549/341; 549/333; 549/373; 549/375; 549/451; 549/453; 558/357; 558/397; 558/428; 558/434; 560/11; 560/118; 562/429; 562/500; 562/506
[58] Field of Search ............... 560/124, 118; 562/506, 562/500; 260/464; 558/428, 434, 357

[56] References Cited

U.S. PATENT DOCUMENTS

| | | | |
|---|---|---|---|
| Re. 27,592 | 3/1973 | Martel | 560/124 |
| 3,567,780 | 3/1971 | Martel | 560/124 |
| 3,711,555 | 1/1973 | Martel | 560/124 |

OTHER PUBLICATIONS

Devos, Tetrahedron Letters, pp. 3911–3914 (1976).
Allinger, "Organic Chemistry", pp. 477–478, 532–537 and 585 (1971).
House, "Modern Synthetic Reactions", 2nd Ed, Benjamin Cummings Publg. Co., Menlo Park, Calif., pp. 598, 602 & 614 (1972).

Primary Examiner—Michael L. Shippen
Attorney, Agent, or Firm—Bierman & Muserlian

[57] ABSTRACT

A process for the preparation of cyclopropane carboxylic acid derivatives of the formula

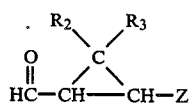

wherein Z is selected from the group consisting of —CN, —COOH and —COOR$_1$, R$_1$ is alkyl of 1 to 6 carbon atoms and R$_2$ and R$_3$ are alkyl of 1 to 4 carbon atoms or taken together with the carbon atom to which they are attached form a carbon homocycle of 3 to 6 carbon atoms comprising reacting at low temperatures in a solvent in the presence of a strong base a compound of the formula

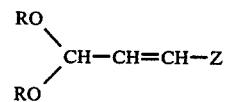

wherein Z has the above definitions and R is alkyl of 1 to 6 carbon atoms or together form a polymethylene of 2 to 3 carbon atoms with a sulfone of the formula

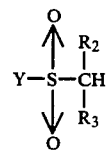

wherein R$_2$ and R$_3$ have the above definitions and Y is an aromatic group followed by aqueous treatment to obtain a compound of the formula

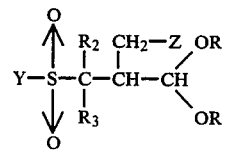

wherein Y, R, R$_2$, R$_3$ and Z have the above definitions, reacting the latter at a low temperature in a solvent with a strong base while letting the temperature rise to obtain a compound of the formula

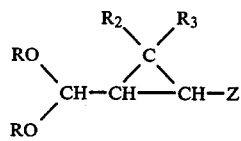

wherein R, R$_2$, R$_3$ and Z have the above definitions of the cis/trans configuration richer in the trans isomer and either reacting the latter when Z is —CN or —COOR$_1$ with a strong base in an aqueous media followed by acidification to obtain a compound of the formula

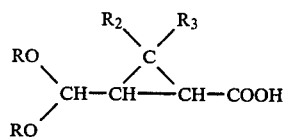

wherein R, R$_2$ and R$_3$ have the above definitions having the same configuration as the compound of formula V or reacting the compound of formula V or Va with an acid agent in an aqueous media to obtain the corresponding compound of formula I with the same configuration as the compound of formula V or Va and optionally treating the latter with a weak base at room temperature to obtain the compound of formula I with a trans configuration which are valuable intermediates for the preparation of esters of cyclopropane carboxylic acid having elevated insecticidal activity.

11 Claims, No Drawings

NOVEL PROCESS FOR PREPARATION OF 1-FURENYL-2,2-DIMETHYL-CYCLOPROPANE CARBOXYLIC ACID DERIVATIVES

PRIOR APPLICATION

This application is a continuation of U.S. patent application Ser. No. 300,927 filed Sept. 10, 1983, now abandoned.

STATE OF THE ART French patent No. 1,507,192 describes a process for the preparation of cyclopropane carboxylic acids by reacting an aryl sulfone in the presence of a base with an alkyl β,β-dimethyl-acrylate with is different from the process of the invention as the compounds of formula I contain an aldehyde group in addition to the carboxylic acid or nitrile group by reacting an alkyl aryl sulfone or cycloalkyl aryl sulfone in the presence of a base with an acrylic derivative containing an aldehyde group protected in the form of a ketal.

U.S. Pat. No. 3,445,499 describes a process starting with an arylsulfonic acid and not a substituted aryl alkyl sulfone of formula III. This means the intermediate products and final products are different from the process of the present invention.

Russian Chem. Reviews, Vol. 44, No. 2 (1975), p. 154–156 describes a process starting with a sulfide or sulfoxide different from the sulfones of formula III under totally different conditions to obtain different compounds.

Our copending, commonly assigned U.S. patent application Ser. No. 246,170 filed Mar. 23, 1981 describes a similar process with a common reaction step with a sulfone of formula III but the final steps are different.

OBJECTS OF THE INVENTION

It is an object of the invention to provide a novel process for the preparation of a compound of formula I in a limited number of steps.

This and other objects and advantages of the invention will become obvious from the following detailed description.

THE INVENTION

The novel process of the invention for the preparation of cyclopropane carboxylic acid derivatives of the formula

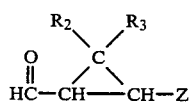
I wherein Z is selected from the group consisting of —CN, —COOH and —COOR$_1$, R$_1$ is alkyl of 1 to 6 carbon atoms and R$_2$ and R$_3$ are alkyl of 1 to 4 carbon atoms or taken together with the carbon atom to which they are attached form a carbon homocycle of 3 to 6 carbon atoms comprises reacting at low temperatures in a solvent in the presence of a strong base a compound of the formula

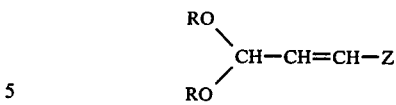
II wherein Z has the above definitions and R is alkyl of 1 to 6 carbon atoms or together form a polymethylene of 2 to 3 carbon atoms with a sulfone of the formula

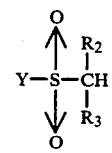
III wherein R$_2$ and R$_3$ have the above definitions and Y is an aromatic group followed by aqueous treatment to obtain a compound of the formula

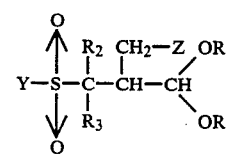
IV wherein Y, R, R$_2$, R$_3$ and Z have the above definitions, reacting the latter at a low temperature in a solvent with a strong base while letting the temperature rise to obtain a compound of the formula

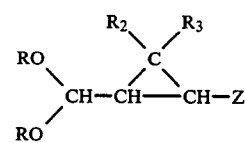
V wherein R, R$_2$, R$_3$ and Z have the above definitions of the cis/trans configuration richer in the trans isomer and either reacting the latter when Z is —CN or —COOR$_1$ with a strong base in an aqueous media followed by acidification to obtain a compound of the formula

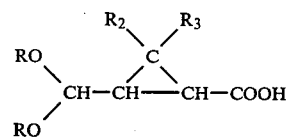
Va wherein R, R$_2$ and R$_3$ have the above definitions having the same configuration as the compound of formula V or reacting the compound of formula V or Va with an acid agent in an aqueous media to obtain the corresponding compound of formula I with the same configuration as the compound of formula V or Va and optionally treating the latter with a weak base at room temperature to obtain the compound of formula I with a trans configuration.

In the above formulae, Z is the group —CN or —COOH or —COOR$_1$ wherein R$_1$ is alkyl of 1 to 6 carbon atoms such as methyl, ethyl, n-propyl, isopropyl and linear or branched butyl, pentyl or hexyl. More generally, Z is an electroattracting group permitting a 1,4-addition of the Michael type.

Examples of R are alkyl of 1 to 6 carbon atoms such as methyl, ethyl, propyl, isopropyl and branched or linear butyl, pentyl or hexyl or polymethylene such as ethylene or propylene. Examples of Y are aromatic groups such as phenyl p-tolyl, p-nitrophenyl or p-chlorophenyl. Examples of $R_2$ and $R_3$ are alkyl of 1 to 4 carbon atoms such as methyl, ethyl, propyl, isopropyl and branched or linear butyl or taken together with the carbon to which they are attached form a cycloalkyl such as cyclopropyl, cyclobutyl, cyclopentyl or cyclohexyl.

In a modification of the process of the invention, the compound of formula IV is not isolated and after the reaction of the compounds of formulae II and III, the temperature of the reaction mixture is allowed to rise to directly obtain the compound of formula V.

In a preferred mode of the process of the invention, Z in the compound of formula II is either —CN or —COOR$_1$ and $R_2$ and $R_3$ are methyl.

In a preferred mode of the process of the invention, the strong base present during the reaction of the compounds of formulae II and III is selected from the group consisting of alkali metal alcoholates, alkali metal hydrides, amide of diisopropylamine, alkali metal amides, aryllithiums and alkyllithium and the solvent is a polar solvent selected from the group consisting of dimethoxyethane, dimethylformamide, tetrahydrofuran, hexamethylphosphorotriamide and mixtures thereof with hydrocarbons such as monocyclic aromatic hydrocarbons or cycloalkanes.

The preferred low temperature for the reaction of the compounds of formulae II and III is $-90°$ to $-30°$ C. and the preferred low temperature for treating the compound of formula IV with a strong base is $-60°$ to $-10°$ C. and the mixture containing the compound of formula IV is preferably allowed to rise to $10°$ to $30°$ C.

In the process of the invention, the strong base reacted with the compound of formula V wherein Z is —COOR$_1$ is preferably an alkali metal hydroxide and the acid agent to hydrolyze the ketal group is preferably selected from the group consisting of sulfuric acid, hydrochloric acid and phosphoric acid. The weak base reacted with the compound of formula I with a cis/-trans mixture rich in the trans form to obtain the compound of formula I with the trans form is preferably an alkali metal carbonate.

The reaction of the compounds of formulae II and III at a low temperature in the presence of a strong base forms the ionic intermediate of the formula

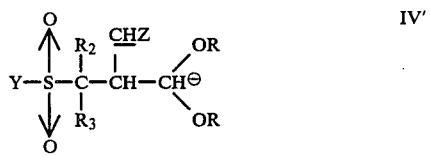

which by protonation yields the sulfone of formula IV.

The treatment of the sulfone of formula IV in an organic solution at a low temperature in the presence of a strong base followed by heating of the reaction mixture yields the compound of formula V rich in the trans form but containing a certain amount of the cis form which optionally is transformed into the compound of formula Va. After hydrolysis of the ketal group followed by treatment with a basic agent, the compounds of formulae V or Va are transformed into a compound of formula I with only the trans form. The compound of formula V may be directly obtained by heating the reaction mixture after reaction of the compounds of formulae II and III in the presence of a strong base.

Isopropyl phenyl sulfone may be prepared by reacting an isopropyl halide in a basic media with an alkali metal phenylsulfinate as follows

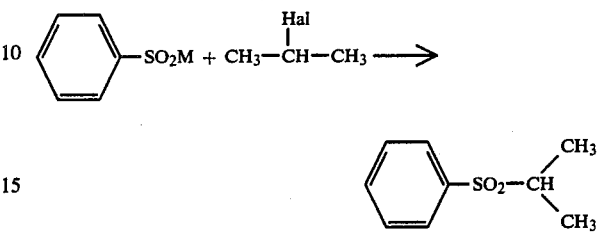

Other sulfones of formula III may be made in an analogous fashion.

In the following examples there are described several preferred embodiments to illustrate the invention. However, it should be understood that the invention is not intended to be limited to the specific embodiments.

EXAMPLE 1 dl trans 3-formyl-2,2-dimethyl-cyclopropane-carbonitrile

STEP A:

4-p-tolylsulfonyl-4-methyl-3-dimethoxymethyl-pentanenitrile 22.5 ml of a 1.75M butyllithium in cyclohexane solution were added at $-30°$ C. to a mixture of 7.79 g of p-tolylisopropyl sulfone in 40 ml of tetrahydrofuran and the mixture was stirred for 15 minutes after which a solution of 5 g of β-cyano-acrolein dimethyl acetal in 30 ml of tetrahydrofuran was slowly added thereto at $-70°$ C. The mixture was stirred at $-70°$ C. for 40 minutes and at $-30°$ C. for 90 minutes and was then poured into iced aqueous sodium dihydrogen phosphate solution. The mixture was extracted with benzene and the organic phase was dried and evaporated to dryness under reduced pressure. The residue was chromatographed over silica gel and was eluted with a 9-1 benzene-ethyl acetate mixture to obtain 8.33 g of 4-p-tolylsulfonyl-4-methyl-3-dimethoxymethylpentanenitrile melting at $99°$ C.

IR Spectrum (chloroform): Absorption at 2240 cm$^{-1}$ (—CN); at 1593 and 1490 cm$^{-1}$ (aromatic ring); at 1307, 1295 and 1142 cm$^{-1}$ (—SO$_2$).

NMR Spectrum (deuterochloroform): Peaks at 1.35 ppm (hydrogens of methyls α-to SO$_2$); at 2.75 ppm (hydrogens α- and β-to —CN); at 2.46 ppm (hydrogens of —CH$_3$ of tolyl); at 3.4 ppm (hydrogens of methyls of CH$_3$O—); at 4.7 ppm (hydrogen on carbon attached to methoxys); at 7.3–7.4 ppm (3- and 5-hydrogens of p-tolyl); at 7.7–7.9 ppm (2- and 6-hydrogens of -tolyl).

STEP B: dl cis trans 3-dimethoxymethyl-2,2-dimethyl-cyclopropane-carbonitrile 1.15 ml of 1.75M of butyllithium in cyclohexane were added at $-40°$ C. to a solution of 0.32 ml of diisopropylamine in 3 ml of tetrahydrofuran and the mixture was stirred for 15 minutes at $25°$ C. and was then cooled to $-35°$ C. A solution of 0.598 g of the product of Step A in 5 ml of tetrahydrofuran was added to the mixture over 10 minutes at −35° C. and the mixture was stirred at 20° C. for 2½ hours and was then poured into iced aqueous sodium dihydrogen phosphate solution. The mixture was extracted with benzene and the organic phase was dried and evaporated to dryness under reduced pressure. The residue was chromatographed over silica gel and was eluted with a 7-3 petroleum ether (b.p.=40°-70° C.)-ether mixture to obtain 0.182 g of dl cis trans 3-dimethoxymethyl-2,2-dimethylcyclopropane-carbonitrile.

STEP C: dl cis trans 3-formyl-2,2-dimethyl-cyclopropane-carbonitrile

A mixture of 0.332 g of the product of Step B, 0.7 ml of methanol and 2.5 ml of N hydrochloric acid solution was refluxed for 2½ hours and was then added to water. The mixture was extracted with methylene chloride and the organic phase was washed with aqueous sodium bicarbonate solution, dried and evaporated to dryness under reduced pressure to obtain 0.222 g of dl cis trans 3-formyl-2,2-dimethyl-cyclopropane-carbonitrile.

IR Spectrum (chloroform): Absorption at 1713 cm$^{-1}$ (—C=O); at 2738 cm$^{-1}$ (CH of aldehyde); at 2240 cm$^{-1}$(—CN).

NMR Spectrum (deuterochloroform): Peaks at 1.3–1.5 ppm (cis derivative) and at 1.27–1.46 ppm (trans derivative) (hydrogens of geminal methyls); at 1.8–2.16 ppm (1- and 3-hydrogens of cyclopropane of cis form); at 2.16–2.26 ppm (1-hydrogen of cyclopropane of trans form); at 2.3–2.4–2.44–2.49 ppm (3-hydrogens of cyclopropane of trans form); 9.6–9.7 ppm (trans form) and 9.5–9.6 ppm (cis form) (hydrogen of —CHO). The NMR spectrum showed that the mixture contained about 70% of the trans form and 30% of the cis form.

STEP D: dl trans 3-formyl-2,2-dimethyl-cyclopropane-carbonitrile

Sodium carbonate was added to a mixture of 5 ml of water, 2 ml of methanol and 0.189 of the product of Step C until the pH was 11-12 and the mixture was stirred at 20° C. for 4 hours and was then extracted with methylene chloride. The organic phase was dried and evaporated to dryness under reduced pressure. The residue was chromatographed over silica gel and was eluted with a 9-1 benzene-ethyl acetate mixture to obtain 0.120 g of pure dl trans 3-formyl-2,2-dimethyl-cyclopropane-carbonitrile.

EXAMPLE 2 dl cis trans 3-dimethoxymethyl-2,2-dimethyl-cyclopropane-carbonitrile

In a modification of the process for the direct obtention of the above compound, 4.5 ml of 1.75M butyllithium in cyclohexane solution were added at −25° C. to a solution of 1.50 g of isopropyl p-tolyl sulfone in 10 ml of tetrahydrofuran and the mixture was stirred at −25° C. for 15 minutes. Then, a solution of 1 g of β-cyano-acrolein dimethylacetal in 7 ml of tetrahydrofuran was added at −70° C. to the mixture and after the temperature returned to 20° C., the mixture was stirred at 20° C. for 3 hours. The mixture was poured into iced aqueous saturated sodium dihydrogen phosphate solution and the mixture was extracted with benzene. The organic phase was dried and evaporated to dryness under reduced pressure. The residue was chromatographed over silica gel and was eluted with a 9-1 benzene-ethyl acetate mixture to obtain 0.427 g of dl cis trans 3-dimethoxymethyl-2,2-dimethyl-cyclopropane-carbonitrile.

EXAMPLE 3

Methyl dl trans-3-dimethoxymethyl-2,2-dimethyl-cyclopropane-1-carboxylate

STEP A: Methyl 4-p-toluenesulfonyl-4-methyl-3-dimethoxymethylpentanoate 3.4 ml of a 1.95M butyllithium in cyclohexane solution were slowly added at −70° C. to a solution of 1.24 g of p-tolyl isopropyl sulfone in 13 ml of tetrahydrofuran and the mixture was stirred at −70° C. for 15 minutes. Then, a solution of 1 g of methyl 4,4-dimethoxy-2-butenoate in 20 ml of tetrahydrofuran was slowly added to the mixture which was stirred at −70° C. for one hour and poured into a aqueous monosodium phosphate solution. The mixture was extracted with methylene chloride and the organic phase was dried and evaporated to dryness under reduced pressure. The residue was chromatographed over silica gel and was eluted with a 1—1 ether-petroleum ether (b.p.=40°-70° C.) mixture to obtain 1.1 g of methyl 4-p-toluenesulfonyl-4-methyl-3-dimethoxymethyl-pentanoate melting at 110° C.

IR Spectrum (chloroform): Absorption at 1732 cm$^{-1}$ (—C=O); at 1600–1495 cm$^{-1}$ (aromatic ring); at 1310–1301–1250 cm$^{-1}$ (SO$_2$); at 690 cm$^{-1}$

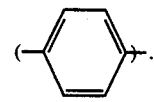

NMR Spectrum (deuterochloroform): Peaks at 1.31–1.35 ppm (hydrogens of geminal methyls α-to SO$_2$); at 2.45 ppm (hydrogens of methyl of p-tolyl); at 3.2–3.3 ppm (hydrogens of methoxy); at 3.7 ppm (hydrogens of methyl of carboxymethyl).

STEP B: Methyl dl trans 3-dimethoxymethyl-2,2-dimethyl-cyclopropane-1-carboxylate 2.36 ml of a 1.75M butyllithium in cyclohexane solution were added at −35° C. to a solution of 0.72 ml of diisopropylamine in 7.2 ml of tetrahydrofuran and the mixture was stirred at −30° C. for 15 minutes and was then cooled to −50° C. A solution of 1.5 g of the product of Step A in 15 ml of tetrahydrofuran was progressively added to the mixture after which the temperature was progressively increased to 20° C. The mixture was heated at 40° C. for 22 hours and was then cooled and poured into iced aqueous monosodium phosphate solution. The mixture was extracted with benzene and the organic phase was dried and evaporated to dryness under reduced pressure. The residue was charmatographed over silica gel and was eluted with a 1-1 ether-petroleum ether (b.p.=40°-70° C.) mixture to obtain 0.141 g of methyl dl trans 3-dimethoxymethyl-2,2-dimethyl-cyclopropane-1-carboxylate.

NMR Spectrum (deuterochloroform): Peaks at 1.21 ppm (hydrogens of geminal methyls); at 1.54–1.62 ppm (1-hydrogen of cyclopropane); at 2.33-2.36-2.41-2.45 ppm (3-hydrogen of cyclopropane); at 3.31 ppm (hydrogens of CH$_3$O—).

EXAMPLE 4 dl trans 2,2-dimethyl-3-formyl-cyclopropane-1-carboxylic acid 10 g of the product of Example 3 were added to a mixture of 100 ml of methanol and 100 ml of aqueous N sodium hydroxide solution and the mixture was stirred at 40° C. for 5 hours. The mixture was acidified to a pH of 1 by addition of dilute hydrochloric acid solution and was stirred at 20° C. for 5 hours. The mixture was extracted with methylene chloride and the organic phase was dried and evaporated to dryness under reduced pressure to obtain 6.5 g of dl trans 2,2-dimethyl-3-formyl-cyclopropane-1-carboxylic acid.

Various modifications of the process of the invention may be made without departing from the spirit or scope thereof and it should be understood that the invention is intended to be limited only as defined in the appended claims.

We claim:

1. A process for the preparation of cyclopropane carboxylic acid derivatives of the formula

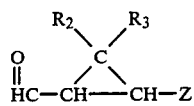   I wherein Z is selected from the group consisting of —CN and —COOR$_1$, R$_1$ is alkyl of 1 to 6 carbon atoms and R$_2$ and R$_3$ are alkyl of 1 to 4 carbon atoms or taken together with the carbon atom to which they are attached form a carbon homocycle of 3 to 6 carbon atoms comprising reacting at low temperatures of —90° to —30° C. in a solvent in the presence of a strong base a compound of the formula

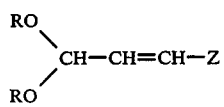   II wherein Z has the above definition and R is alkyl of 1 to 6 carbon atoms or together form a polymethylene of 2 to 3 carbon atoms with a sulfone of the formula

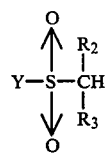   III wherein R$_2$ and R$_3$ have the above definitions and Y is an aromatic group followed by aqueous treatment to obtain a compound of the formula

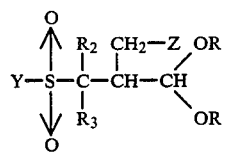   IV wherein Y, R, R$_2$, R$_3$ and Z have the above definitions, reacting the latter at a low temperature in a solvent with a strong base while letting the temperature rise to obtain a compound of the formula

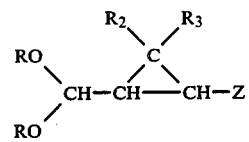   V wherein R, R$_2$, R$_3$ and Z have the above definitions of the cis/trans configuration richer in the trans isomer and reacting the latter with a strong base in an aqueous media followed by acidification to obtain a compound of the formula

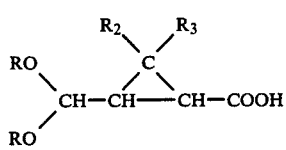   Va wherein R, R$_2$ and R$_3$ have the above definitions having the same configuration as the compound of formula I, reacting the compound of formula Va with an acid agent in an aqueous media to obtain the corresponding acid of formula I with the same configuration as the compound of formula Va and optionally treating the latter with a weak base at room temperature to obtain the acid of formula I with a trans configuration.

2. A process for the preparation of cyclopropane carboxylic acid derivatives of the formula

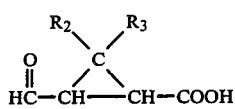   I wherein R$_1$ is alkyl of 1 to 6 carbon atoms and R$_2$ and R$_3$ are alkyl of 1 to 4 carbon atoms or taken together with the carbon atom to which they are attached form a carbon homocycle of 3 to 6 carbon atoms comprising reacting at low temperatures of —90° to —30° C. in a solvent in the presence of a strong base a compound of the formula

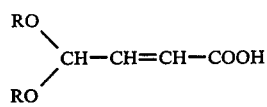   II wherein R is alkyl of 1 to 6 carbon atoms or together form a polymethylene of 2 to 3 carbon atoms with a sulfone of the formula

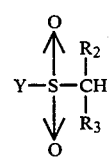   III wherein R$_2$ and R$_3$ have the above definitions and Y is an aromatic group followed by aqueous treatment to obtain a compound of the formula

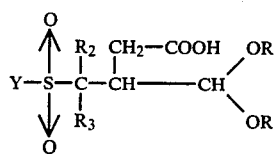

wherein Y, R, $R_2$, $R_3$ and Z have the above definitions, reacting the latter at a low temperature in a solvent with a strong base while letting the temperature rise to obtain a compound of the formula

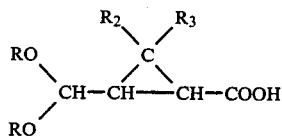

wherein R, $R_2$, $R_3$ and Z have the above definitions of the cis/trans configuration richer in the trans isomer and reacting the compound of formula V with an acid agent in an aqueous media to obtain the corresponding compound of formula I with the same configuration as the compound of formula V and optionally treating the latter with a weak base at room temperature to obtain the compound of formula I with a trans configuration.

3. The process of claim 1 or 2 wherein the temperature of the reaction mixture of the reaction of the compounds of formulae II and III at a low temperature is allowed to rise to obtain directly the compound of formula V without isolation of the compound of formula IV.

4. The process of claim 1, wherein $R_2$ and $R_3$ are methyl.

5. The process of claim 1 or 2 wherein the strong base present in the reaction of the compounds of formulae II and III is selected from the group consisting of alkali metal alcoholates, alkali metal hydrides, amide of diisopropylamine, alkali metal amides, aryllithium and alkyllithium.

6. The process of claim 5 wherein the solvent for the reaction is a polar solvent selected from the group consisting of dimethoxyethane, dimethylformamide, tetrahydrofuran, hexamethylphosporotriamide and mixtures thereof with hydrocarbons.

7. The process of claim 1 wherein the treatment of the compound of formula IV with a strong base is effected at $-60°$ to $-10°$ C.

8. The process of claim 1 or 2 wherein the temperature to which the mixture containing the compound of formula IV is allowed to rise to $+10°$ to $30°$ C.

9. The process of claim 1 wherein the strong base reacted with a compound of formula V wherein Z is —CN or —$COOR_1$ is an alkali metal hydroxide.

10. The process of claim 1 wherein the acid hydrolysis of the ketal is effected with an acid selected from the group consisting of sulfuric acid, hydrochloric acid and phosphoric acid.

11. The process of claim 1 or 2 wherein the weak base is an alkali metal carbonate.

* * * * *